United States Patent [19]

Kawakami et al.

[11] 4,238,410

[45] Dec. 9, 1980

[54] PROCESS FOR PRODUCING MAGNESIUM SALT OF OLEFIN SULFONIC ACID

[75] Inventors: Akira Kawakami, Sakura; Haruo Ohkouchi, Chiba; Yoshio Aoki, Tokyo; Kyozo Kitano, Chiba, all of Japan

[73] Assignee: The Lion Fat and Oil Co., Ltd., Tokyo, Japan

[21] Appl. No.: 905,001

[22] Filed: May 11, 1978

[30] Foreign Application Priority Data

May 31, 1977 [JP] Japan .................................. 52-63515

[51] Int. Cl.³ .......................................... C07C 143/16
[52] U.S. Cl. .............................................. 260/513 R
[58] Field of Search ................................... 260/513 R

[56] References Cited

U.S. PATENT DOCUMENTS

| | | | |
|---|---|---|---|
| 2,511,043 | 6/1950 | Busch ............................... | 260/513 R |
| 4,146,551 | 3/1979 | Kawakami et al. .............. | 260/513 R |

OTHER PUBLICATIONS

Colgate-Palmolive, "Belgian Patents Report No. 5" (1968), General Organic - p. 3. (Belgian Patent 702163).

Primary Examiner—Joseph E. Evans
Attorney, Agent, or Firm—Armstrong, Nikaido, Marmelstein & Kubovcik

[57] ABSTRACT

Disclosed is a process for producing the magnesium salt of an olefin sulfonic acid comprising the steps of:

sulfonating and neutralizing an olefin having 10 to 20 carbon atoms, and; then, hydrolyzing sultone contained in the resulting neutralization product in the presence of,
  (a) magnesium hydroxide, magnesium oxide and a mixture thereof and
  (b) an additive selected from the group consisting of benzoic acid, citric acid, malic acid, phosphoric acid, polyphosphoric acid and water-soluble salts thereof, at a temperature within the range of from 110° C. to 180° C.

5 Claims, No Drawings

PROCESS FOR PRODUCING MAGNESIUM SALT OF OLEFIN SULFONIC ACID

BACKGROUND OF THE INVENTION

1. Field of the Invention

The present invention relates to a process for producing the magnesium salt of olefin sulfonic acids, and more specifically, it relates to a process for producing the magnesium salt of olefin sulfonic acids which contain only a small amount of unreacted magnesium compounds and do not cause the generation of foreign odor and color change.

2. Description of the Prior Art

Olefin sulfonic acids have been heretofore used as a surface-active agent, generally in the form of the sodium salt. However, recently, the magnesium salts of olefin sulfonic acids have become of major interest as a surface-active agent due to the fact that they have an excellent frothing property.

In the production of the magnesium salts of olefin sulfonic acids, when magnesium hydroxide and/or magnesium oxide are employed as a neutralizing agent, there are disadvantages in that extremely long operations for the neutralization of a alkene sulfonic acids and for the hydrolysis of sultone contained in the neutralization products are required. This is because magnesium hydroxide and oxide are only slightly soluble in water. The above-mentioned neutralization reaction can be more or less accelerated by heating the reaction system or by vigorously agitating the reaction system. However, in order to accelerate the above-mentioned hydrolysis reaction, the heating or the vigorous agitation of the reaction system is not practically applicable, due to the fact that acidification of the reaction system occurs. That is to say, the hydrolysis of the sultone comprises the ring opening (or cleavage) reaction of the sultone ring, and the neutralization reaction of the hydroxyalkane sulfonic acids and alkene sulfonic acids which are formed by the cleavage reaction of the sultone ring. However, if the dissolving rate of the magnesium compound necessary for the neutralization reaction is slow, the reaction system necessarily becomes acidic since the cleavage reaction is faster than the neutralization reaction.

As is well-known, the hydrolysis of the sultone under an acidic condition causes the generation of foreign odor and color change in the reaction products. It has not been proposed heretofore that the hydrolysis of the sultone can be accelerated without causing the above-mentioned problems. In the case where the sultone is hydrolyzed in the presence of a large excess of the magnesium compound, the hydrolysis can be somewhat accelerated and the generation of foreign odor and color change can be more or less depressed. However, this method is still not preferable, because a large amount of the unreacted magnesium compound remains, as an insoluble material, in the reaction products.

SUMMARY OF THE INVENTION

The objects of the present invention are to obviate the above-mentioned disadvantage of the conventional process for producing the magnesium salts of olefin sulfonic acids, and to provide a process for producing the magnesium salts of olefin sulfonic acids, which is capable of accelerating the hydrolysis of the sultone without causing the acidification of the reaction system and producing the reaction product containing, if any, only a small amount of the unreacted magnesium compound or compounds.

Other objects and advantages of the present invention will be apparent from the following description.

In accordance with the present invention, the magnesium salts of olefin sulfonic acids are produced in a process comprising the steps of sulfonating and neutralizing an olefin having 10 to 20 carbon atoms and then heating the resulting neutralization product in the presence of magnesium hydroxide, magnesium oxide and a mixture thereof to thereby hydrolyze sultone present in the neutralization product; wherein the hydrolysis of the sultone is carried out in the presence of at least one additive selected from the group consisting of benzoic acid, citric acid, malic acid, phosphoric acid, polyphosphoric acid and water-soluble salts thereof, at a temperature of within the range from 110° C. to 180° C.

DESCRIPTION OF THE PREFERRED EMBODIMENTS

The olefins employed as a starting material in the present invention include $\alpha$-olefins having 10 to 20 carbon atoms, such as dodecene-1, tetradecene-1, hexadecene-1, octadecene-1 and their mixtures; internal olefins having 10 to 20 carbon atoms, such as tetradecene-2, tetradecene-3, tetradecene-4, hexadecene-2, hexadecene-3, hexadecene-5, hexadecene-8, octadecene-2, octadecene-3, octadecene-6 and their mixtures and; vinylidene type olefins having 10 to 20 carbon atoms, such as 2-methyl-dodecene-1, 2-butyl-dodecene-1, 2-hexyl-decene-1, 2-hexyl-dodecene-1 and their mixtures. Among these olefins, $\alpha$-olefins and internal olefins are preferable for use in the present invention.

According to the present invention, the olefins are first sulfonated by any known procedure, for example, with gaseous sulfur trioxide diluted by an inert gas. The sulfonation products of the olefins can be neutralized in the known manner. Thus, any known neutralizing agent and neutralizing conditions for converting acids, such as alkene sulfonic acids, contained in the sulfonation products of olefins to the corresponding salts thereof can be applied to the neutralization step of the present invention. The use of magnesium hydroxide and/or magnesium oxide as a neutralizing agent in the present invention is preferable.

The neutralized sulfonation products of olefins are then hydrolyzed in the presence of magnesium hydroxide and/or magnesium oxide. According to the present invention this hydrolysis is effectively carried out also in the presence of at least one additive, at a temperature within the range of from 110° C. to 180° C. Said additives include benzoic acid, citric acid, malic acid and the water-soluble salt thereof (e.g. sodium benzoate, sodium citrate, sodium malate, potassium benzoate and alkanol amine salt of benzoic acid, and; phosphoric acid, polyphosphoric acid and the water-soluble salts thereof (e.g. sodium phosphate, sodium pyrophosphate, sodium tripolyphosphate and potassium pyrophosphate). Thus, it has been found that, since an additive selected from benzoic acid, citric acid, malic acid, phosphoric acid, polyphosphoric acid and any water-soluble salts thereof has a function to accelerate the dissolving rate of magensium hydroxide and magnesium oxide into water, the sultone contained in the neutralization products of the sulfonated olefins can be hydrolyzed without causing the acidification of the reaction system when the hydrolysis of the sultone is carried out in the presence of both said additive and magnesium hydroxide and/or oxide.

The amount of the additive is 0.5% by weight or more, and more preferably within the range of approximately 1 to approximately 10% by weight, based on the weight of the magnesium salt of the olefin sulfonic acids to be produced from the sulfonation products of the olefins. When the amount of the additive is less than 0.5% by weight, the dissolving rate of magnesium hydroxide and/or oxide cannot be practically improved. The additive can be added to the reaction system either before or after the neutralization reaction if it is added prior to the hydrolysis reaction. It is, therefore, convenient to add said additive to the sulfonation products of the olefins prior to the neutralization step. This is because, when magnesium hydroxide and/or magnesium oxide are used as a neutralizing agent, said additive can also accelerate the dissolving rate of the neutralizing agent, so that the neutralization rate is increased.

The magnesium hydroxide and/or magnesium oxide can be used in an amount sufficient to completely convert the olefin sulfonic acids to the corresponding magnesium salts thereof. Although no critical amount of the magnesium hydroxide and/or magnesium oxide exists, the preferable amount is within the range of from the chemically equivalent amount to approximately 1.2 times thereof.

The hydrolysis reaction can be practically carried out at a temperature within the range of from approximately 110° C. to approximately 180° C. When the temperature is less than 110° C., the rate of the hydrolysis reaction is too slow for practical use. On the other hand, when the temperature is more than 180° C., the coloring or, in the extreme case, foreign odor, of the hydrolyzate is generated.

As is clear from the above description, according to the present invention, even if magnesium hydroxide and/or magnesium oxide only slightly soluble in water are used, the reaction system in which the sultone is hydrolyzed is not acidified and, moreover, the hydrolyzing rate can be accelerated. Accordingly, the utilization of the present invention can effectively produce magnesium salts of olefin sulfonic acids which do not cause the generation of foreign odor and color changes.

In order to further illustrate the present invention, the specific examples set forth below are presented. It is to be understood, however, that this is merely intended in an illustrative and not limitative sense. In the examples, all percents are by weight, unless otherwise indicated.

EXAMPLES 1 to 7

$C_{14}$ α-olefin sulfonic acid were prepared by sulfonating $C_{14}$ α-olefins with gaseous sulfur trioxide diluted by using a falling film type sulfonation reactor as disclosed in, for example, U.S. Pat. No. 4,036,596 under the conditions of mole ratio of $SO_3$/olefin of 1.14 and a temperature of 55° to 60° C. 200 g of the $C_{14}$ α-olefin sulfonates thus obtained were charged into a 1000 ml beaker, and magnesium hydroxide or oxide and the additives listed in Table 1, below, were added thereto, in the amounts shown in Table 1, to neutralize the acids contained in the sulfonate. Thereafter, the sultones presented in the neutralization products were hydrolyzed in a 1000 ml autoclave under the conditions set forth in Table 1 to give an aqueous solution containing the magnesium salts of the olefin sulfonic acids. In Examples 1 to 3, no additive was used for the purpose of comparison.

The aqueous solution containing the magnesium salts of the olefin sulfonic acids (AOS-½ Mg) obtained in each Example was tested with respect to odor and color. The odor of the aqueous solution was olganoleptically tested and evaluated as follows.
O: no acidic odor
Δ: slightly acidic odor
X: heavy acidic odor
The color of the aqueous solution was checked by the naked eye and evaluated as follows.
O: slightly yellow
Δ: brown
X: black
The overall evaluation result was determined from the results of color check and odor test, in view of the hydrolysis time, and rated as follows.
O: good
X: poor
The results are shown in Table 1.

TABLE 1

| Example No. | 1* | 2* | 3* | 4 | 5 | 6 | 7 |
|---|---|---|---|---|---|---|---|
| Neutralizing Agent (g) | | | | | | | |
| Mg(OH)$_2$ | 24.1 | 24.1 | 24.1 | 24.1 | 24.1 | 24.1 | |
| MgO | | | | | | | 16.6 |
| Concentration of Neutralizing Agent (%) | 6.5 | 6.5 | 6.5 | 6.6 | 6.6 | 6.6 | 4.6 |
| Additive (g) | | | | | | | |
| Benzoic Acid | | | | 6 | | | |
| Sodium Benzoate | | | | | 6 | | |
| Citric Acid | | | | | | 6 | 6 |
| Hydrolysis Temperature (°C.) | 120 | 130 | 140 | 140 | 140 | 140 | 140 |
| Hydrolysis Time (min) | 120 | 60 | 20 | 20 | 20 | 20 | 20 |
| Property of Resultant Aqueous AOS-½Mg Solution | | | | | | | |
| Odor | O | Δ | X | O | O | O | O |
| Color | O | Δ | X | O | O | O | O |
| Overall Evaluation | X | X | X | O | O | O | O |

*Comparative Example

Examples 8 to 13

The hydrolysis tests were carried out in the same manner as in the previous Examples 1 to 7, except that 200 g of the suefonates of α-olefins, having 12 to 14 carbon atoms, were used. The used amounts of the neutralizing agent and additives, as well as the hydrolysis conditions, are shown in Table 2 below.

The aqueous solutions containing the magnesium salts of the olefin sulfonic acids (AOS-½ Mg) were evaluated by the method described in Examples 1 to 7. The results are shown in Table 2.

TABLE 2

| Example No. | 8* | 9* | 10* | 11 | 12 | 13 |
|---|---|---|---|---|---|---|
| Neutralizing Agent (g) | | | | | | |
| Mg(OH)$_2$ | 25.6 | 25.6 | 25.6 | 25.6 | 25.6 | 25.6 |
| Concentration of Neutralizing Agent (%) | 8.6 | 8.6 | 8.6 | 8.8 | 8.8 | 8.8 |
| Additive (g) | | | | | | |
| Sodium Citrate | | | | 6 | | |
| Malic Acid | | | | | 6 | |
| Sodium Phosphate | | | | | | 6 |
| Hydrolysis Temperature (°C.) | 110 | 120 | 130 | 140 | 140 | 140 |
| Hydrolysis Time (min) | 200 | 120 | 60 | 20 | 20 | 20 |
| Property of Resultant Aqueous AOS-½Mg Solution | | | | | | |
| Odor | O | Δ | X | O | O | O |
| Color | O | Δ | X | O | O | O |
| Overall Evaluation | X | X | X | O | O | O |

*Comparative Example

Examples 14 to 20

The hydrolysis tests were carried out in the same manner as in the previous Examples 1 to 7, except that 200 g of the sulfonates of α-olefins, having 16 to 18 carbon atoms, were used. The used amounts of the neutralizing agent and additives as well as the hydrolysis conditions are shown in Table 3, below.

The aqueous solutions containing the magnesium salts of the olefin sulfonic acids (AOS-½ 1Mg) were evaluated by the method described in Examples 1 to 7. The results are shown in Table 3.

TABLE 3

| Example No. | 14* | 15* | 16* | 17 | 18 | 19 | 20 |
|---|---|---|---|---|---|---|---|
| Neutralizing Agent (g) | | | | | | | |
| Mg(OH)$_2$ | 21.1 | 21.1 | 21.1 | 21.1 | 21.1 | 21.1 | |
| MgO | | | | | | | 14.6 |
| Concentration of Neutralizing Agent (%) | 5.7 | 5.7 | 5.7 | 5.8 | 5.8 | 5.8 | 4.0 |
| Additive (g) | | | | | | | |
| Sodium Benzoate | | | | 8 | | | |
| Pyrophosphoric Acid | | | | | 8 | | |
| Sodium Tripolyphosphate | | | | | | 8 | |
| Sodium Citrate | | | | | | | 6 |
| Hydrolysis Temperature (°C.) | 120 | 130 | 140 | 140 | 140 | 140 | 140 |
| Hydrolysis Time (min) | 120 | 60 | 20 | 20 | 20 | 20 | 20 |
| Property of Resultant Aqueous AOS-½Mg Solution | | | | | | | |
| Odor | O | Δ | X | O | O | O | O |
| Color | O | Δ | X | O | O | O | O |
| Overall Evaluation | X | X | X | O | O | O | O |

*Comparative Example

As is clearly indicated in Tables 1, 2 and 3, in the cases where the additives of the present invention were employed, aqueous solutions of the magnesium salts of olefin suefonic acids having no odor and no color were obtained for a short hydrolysis time of approximately 20 minutes. Contrary to this, when no additive of the present invention was used, a long hydrolysis time was required for obtaining a good aqueous solution of the magnesium salts of olefin sulfonic acids, as in Example 1, 8 or 14. When a short hydrolysis time was employed in the absence of the additives of the present invention, the generation of foreign odor and color change appeared, as in Example 2, 3, 9, 10, 15 or 16.

What we claim is:

1. In a process for producing the magnesium salt of an olefin sulfonic acid in an aqueous medium comprising the steps of:
   sulfonating and neutralizing an olefin having 10 to 20 carbon atoms, and; then
   heating the resulting neutralization product in the presence of magnesium hydroxide, magnesium oxide or a mixture thereof to thereby hydrolyze sultone present in the neutralization product;
   the improvement wherein the hydrolysis of the sultone is carried out in the presence of at least one additive selected from the group consisting of benzoic acid, citric acid, malic acid, and water-soluble salts thereof, at a temperature within the range of from 110° C. to 180° C.

2. The process as claimed in claim 1, wherein the olefin is sulfonated with gaseous sulfur trioxide diluted by an inert gas.

3. The process as claimed in claim 1, wherein the sulfonation product of the olefin is neutralized with magnesium hydroxide, magnesium oxide or a mixture thereof.

4. The process as claimed in claim 1, wherein the amount of the additive is not less than 0.5% weight, based on the weight of the magnesium salt of the olefin sulfonic acid to be produced.

5. The process as claimed in claim 4, wherein the amount of the additive is within the range of from 1 to 10% by weight, based on the weight of the magnesium salt of the olefin sulfonic acid to be produced.

* * * * *